(12) United States Patent
Weiner et al.

(10) Patent No.: US 11,925,397 B2
(45) Date of Patent: Mar. 12, 2024

(54) SYSTEM AND METHOD FOR BONE FIXATION

(71) Applicant: Nextremity Solutions, Inc., Warsaw, IN (US)

(72) Inventors: Lon S. Weiner, Warsaw, IN (US);
Stuart D. Katchis, Warsaw, IN (US);
John R. Pepper, Warsaw, IN (US);
Ryan Schlotterback, Warsaw, IN (US);
Greg Denham, Warsaw, IN (US)

(73) Assignee: MEDARTIS AG, Basel (CH)

(*) Notice: Subject to any disclaimer, the term of this patent is extended or adjusted under 35 U.S.C. 154(b) by 0 days.

(21) Appl. No.: 17/358,706

(22) Filed: Jun. 25, 2021

(65) Prior Publication Data

US 2021/0401477 A1 Dec. 30, 2021

Related U.S. Application Data

(60) Provisional application No. 63/185,761, filed on May 7, 2021, provisional application No. 63/115,460, filed on Nov. 18, 2020, provisional application No. 63/043,841, filed on Jun. 25, 2020.

(51) Int. Cl.
*A61B 17/82* (2006.01)
*A61B 17/00* (2006.01)
*A61B 17/56* (2006.01)

(52) U.S. Cl.
CPC .... *A61B 17/82* (2013.01); *A61B 2017/00477* (2013.01); *A61B 2017/564* (2013.01)

(58) Field of Classification Search
CPC .................................................... A61B 17/82
See application file for complete search history.

(56) References Cited

U.S. PATENT DOCUMENTS

| | | | |
|---|---|---|---|
| 5,190,545 | A | 3/1993 | Corsi et al. |
| 5,665,089 | A | 9/1997 | Dall et al. |
| 5,902,305 | A | 5/1999 | Beger et al. |
| 5,993,452 | A | 11/1999 | Vandewalle |
| 6,761,720 | B1 | 7/2004 | Senegas |
| 7,229,444 | B2 | 6/2007 | Boyd |
| 7,731,718 | B2 | 6/2010 | Schwammberger et al. |
| 8,685,025 | B2 | 4/2014 | Anapliotis |
| 8,764,809 | B2 | 7/2014 | Lorenz et al. |

(Continued)

FOREIGN PATENT DOCUMENTS

| | | |
|---|---|---|
| CN | 204484284 U | 7/2015 |
| CN | 109223152 A | 1/2019 |

(Continued)

OTHER PUBLICATIONS

UKIPO Search Report dated Dec. 23, 2021.

(Continued)

*Primary Examiner* — Sameh R Boles
(74) *Attorney, Agent, or Firm* — Heslin Rothenberg Farley & Mesiti P.C.; Victor A. Cardona, Esq.

(57) ABSTRACT

A system for fixating a bone includes a buckle having a plurality of lock bars and a hook. A cord may connect the hook with an opposite end of the buckle and around a bone. The buckle may include lock bars on the opposite end of the buckle to receive the cord and allow a frictional resistance to a loosening of the cord around the bone to facilitate a reduction of a fracture of the bone.

4 Claims, 19 Drawing Sheets

(56) References Cited

U.S. PATENT DOCUMENTS

| | | |
|---|---|---|
| 9,138,245 B2 | 9/2015 | Mebarak |
| 9,693,812 B2 | 7/2017 | Zeetser et al. |
| 10,966,764 B2 | 4/2021 | McCormick |
| 2008/0234679 A1 | 9/2008 | Sarin et al. |
| 2014/0018807 A1* | 1/2014 | Foerster ............... A61B 17/08 606/74 |
| 2017/0181780 A1 | 6/2017 | Cremer et al. |
| 2018/0161083 A1 | 6/2018 | Kobayashi |
| 2019/0099206 A1 | 4/2019 | Senegas |
| 2019/0133653 A1 | 5/2019 | Swarts |

FOREIGN PATENT DOCUMENTS

| | | |
|---|---|---|
| CN | 209595876 U | 11/2019 |
| DE | 20203174 U1 | 7/2002 |
| GB | 2257913 A | 1/1993 |
| JP | 2018509276 A | 4/2018 |
| KR | 20160058515 A | 5/2016 |
| WO | 9318716 A1 | 9/1993 |
| WO | 2006135935 A1 | 12/2006 |

OTHER PUBLICATIONS

"Locking Plate Fixation of Periprosthetic Femur Fractures with and without Cerclage Wires", N.A. Ebraheim, MD, 2013 Chinese Orthopaedic Association and Wiley Publishing Asia Pty Ltd, pp. 183-187.

"Vascular complication after percutaneous femoral cerclage wire" M. Ehlinger, Orthopaedics & Traumatology: Surgery & Research 104 (2018), pp. 377-381.

UK Search Report dated Dec. 8, 2020.

Japanese Patent Application No. 2021-105275 First Office Action dated Oct. 20, 2023, 6 pp.

* cited by examiner

SYSTEM AND METHOD FOR BONE FIXATION

CROSS-REFERENCE TO RELATED APPLICATIONS

The present application claims priority to U.S. Provisional Application Ser. No. 63/043,841 filed on Jun. 25, 2020, U.S. Provisional Application No. 63/115,460 filed Nov. 18, 2020, and U.S. Provisional Application No. 63/185,761 filed May 7, 2020, all of which are incorporated herein by reference in their entireties.

The present application is related to U.S. application Ser. No. 16/910,328 filed Jun. 24, 2020, which claims the benefit of U.S. Provisional Application Ser. No. 62/865,676 filed Jun. 24, 2019, and U.S. Provisional Application No. 62/905,017 filed Sep. 24, 2019, which are incorporated herein by reference in their entireties.

FIELD OF THE INVENTION

This application relates generally to apparatuses, devices, and methods for bone fixation and more particularly to apparatuses, devices, and methods for cerclage related to skeletal fracture fixation and instrumentation to facilitate fracture reduction.

BACKGROUND

Femoral fractures may occur naturally or iatrogenically during total hip arthroplasty. Depending on the fracture pattern, cerclage alone, cerclage with a plate or plates, cerclage with a strut, cerclage with an extended hip stem, or cerclage with a combination of plates, struts, and/or extended hip stems may be used for bone fixation. However, a problem with cerclage is that it may create poor bone unions without using additional support devices. In particular with total hip arthroplasty using additional support may not be desirable or possible. With femoral fractures, there may be a high load on the cerclage wires resulting in adjacent boney erosion and loss of fixation due to wire migration.

Fracture reduction of long bones often involves realigning spiral fractures and multiple pieces. Bone clamps are often hinged devices (e.g., pliers) with specialized tips or spurs to grab (e.g., engage and hold) bone. The closing of such a clamp puts force on the fragments and pushes them closer together. Limits of traditional clamps are they produce forces linearly, or very close to linearly. Such clamps may also be bulky when multiple clamps are used, as is common, access to a fracture site for placement of hardware (e.g., plates or screws) may be is restricted. Also, single plane forces produced by a clamp cannot adequately reduce some fractures. Further, clamps must be removed after fixation, and sometime loss of reduction and malalignment may occur due to such removal.

In another example, solid cerclage wire has been used to provide circumferential forces to reduce fractures. Use of such wire has some drawbacks, including the wire may be so stiff that manipulating the wire may be very difficult. Also, if the wire is not initially placed ideally, reforming the wire to fit in another location is nearly impossible. Further, the traditional method of tensioning solid cerclage wire involves twisting the ends in a tight spiral. This required specialized bulky tools, and the resulting twisted wire may be extremely stiff and often cannot be flattened to either work around. If the twisted wire is left in place, the wire may irritate soft tissues. These limitations have seen the use of solid temporary wire fixation drop to such that this method is rarely used.

There is a need for a device that provides improved bone unions while minimizing boney erosion and loss of fixation due to wire migration.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention. Thus, all the implementations described below are exemplary implementations provided to enable persons skilled in the art to make or use the embodiments of the disclosure and are not intended to limit the scope of the disclosure, which is defined by the claims.

The following description references systems, methods, and apparatuses for use in femoral fixation. However, those possessing an ordinary level of skill in the relevant art will appreciate that fixation of other bones are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to fixation related to any bone.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
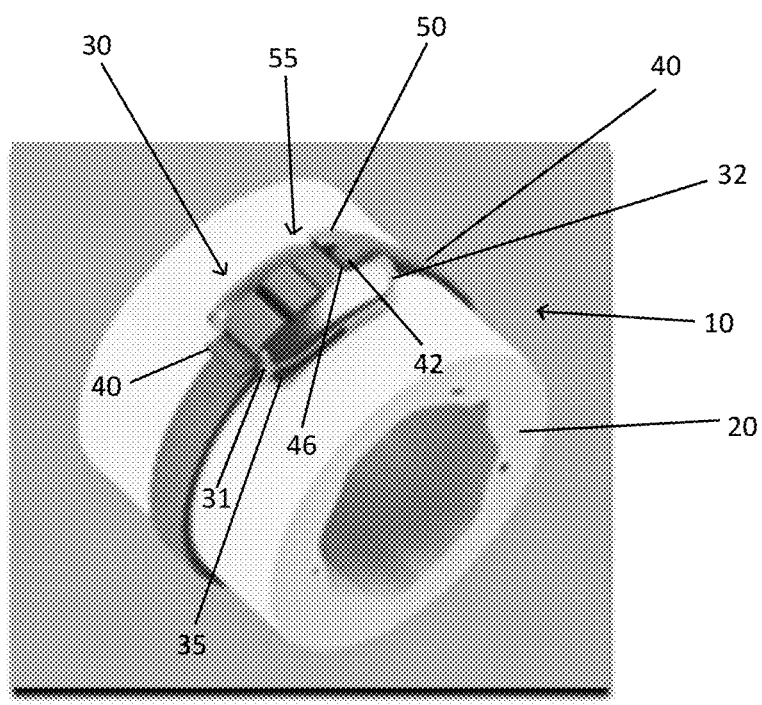
FIG. 1 is a perspective view of a system for fixing bone including a buckle and cord in accordance with the present invention.

A system 10 for fixating or reducing a bone 20 may include a connector or buckle 30 connected to a strap, belt or cord 40 extending around bone 20, as depicted in FIG. 1.

Figure 2:
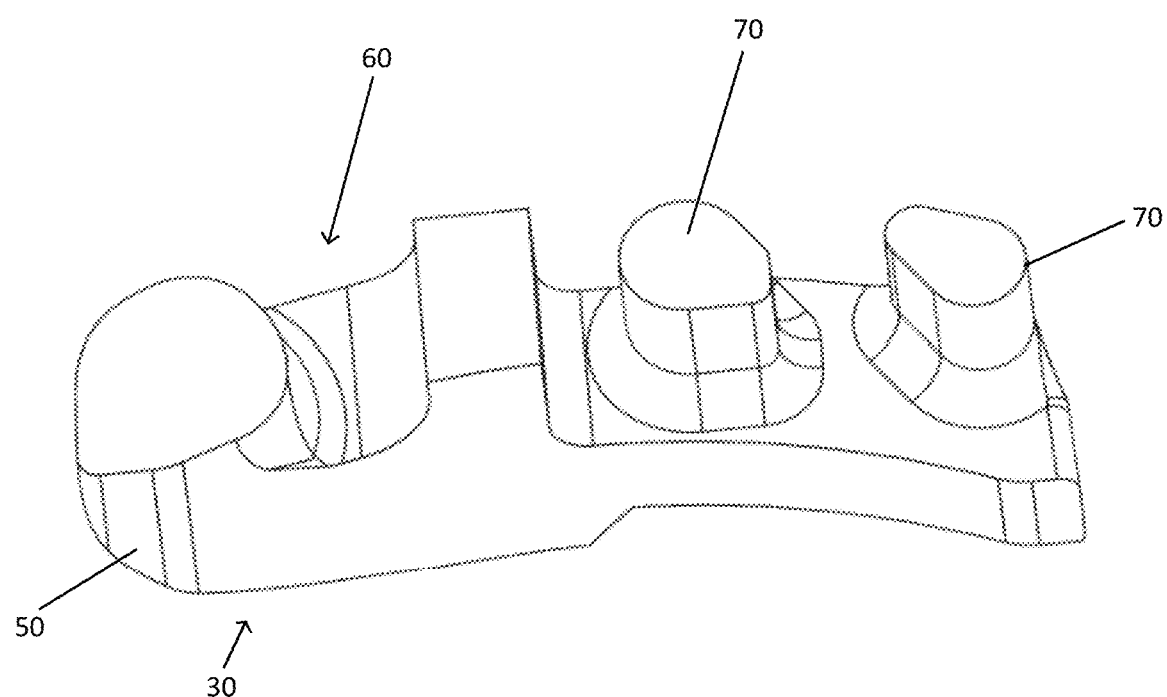
FIG. 2 is a cross-sectional view of a portion of the buckle of FIG. 1 including locking bars.
Figure 3:
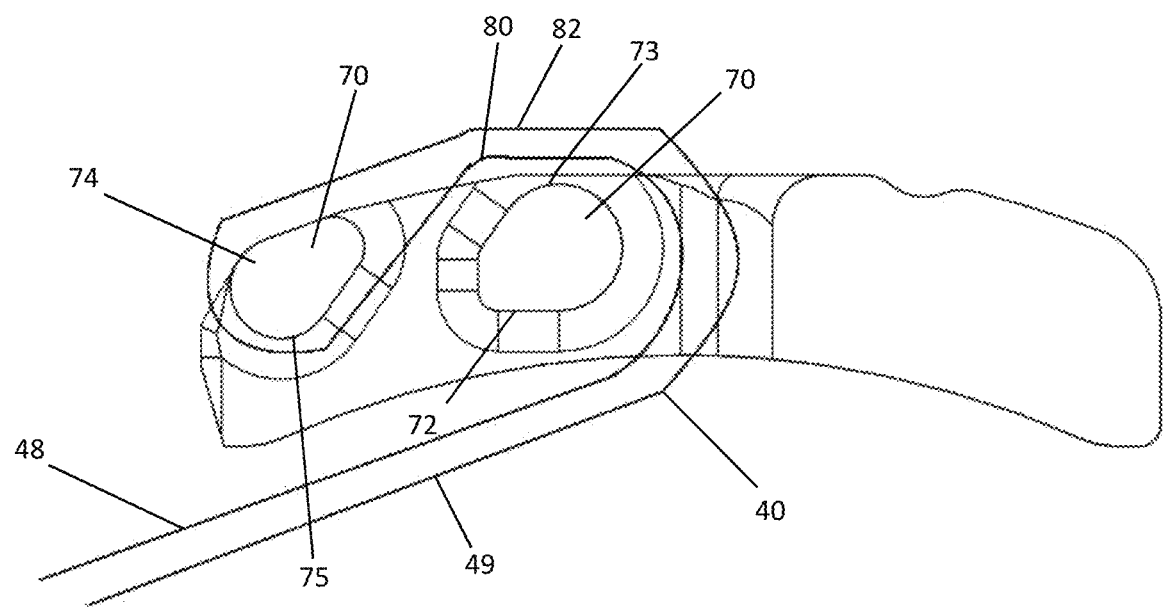
FIG. 3 is a side cross-sectional view of the buckle of FIG. 1 including locking bars and showing a path of the cord of FIG. 1 around the locking bars.
Figure 4:
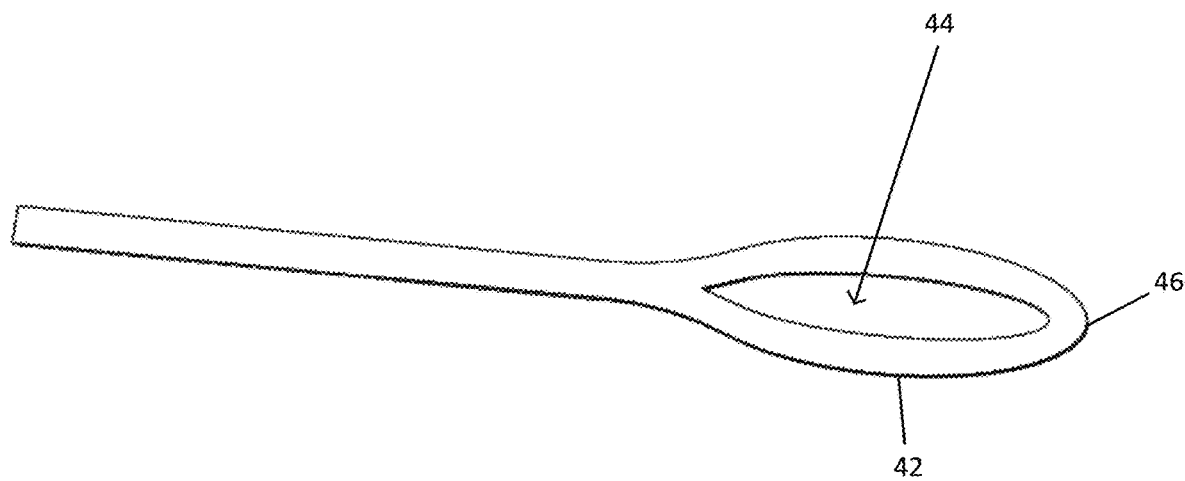
FIG. 4 is a side view of a distal end of the cord of FIG. 1 including a loop for attaching to the buckle.

Buckle 30 may include a plurality of lock bars 70 and a connecting end or hook 50 as depicted cross-sectionally in FIGS. 2-3. Lock bars may have a cross-sectional tear drop shape as depicted in the figures or could have a cross-sectional rounded shape. Hook 50 may be located at a distal end of buckle 30 and may have an opening 55 to allow a cord (e.g., cord 40) to pass therethrough into a receiving cavity 60 bounded by interior surfaces of hook 50. Cord 40 may have a loop 42 connectable to a distal portion 32 of buckle 30 when an opening 44 of loop 42 receives distal portion therein. When connected to buckle 30, a distal end 46 of cord 40 may be received in cavity 60. Cord 40 may also be connected to buckle 30 in other ways besides a loop, such as a knot, a ferrule, a non-eye splice, hitch or embedded internal stopper.

Buckle 30 could be made of stainless steel, surgical grade plastic, Titanium, PEEK, or Cobalt Chrome, for example. Also, cord 40 may be made of a material that may be left in a body for a period of time to allow a bone to heal, such as an Ultra-High Molecular Weight Polyethylene (UHMWPE), for example. Cord 40 may be a 50 cm tape with a width of 3.5 mm and a thickness of 0.6 mm, for example. Further cord 40 may be flexible (e.g., a suture tape) and may be made from strands, or braided stranded, of fine wires of metal or metallic alloy, such as cobalt chrome, stainless steel, titanium and titanium alloys.

A proximal end 48 of cord 40 may be connected to a proximal end 31 of buckle 30. For example, cord 40 may be connected to lock bars 70 as depicted in FIGS. 2-3. After extending around bone 20 as depicted in FIG. 1, cord 40 may extend distally toward hook 50 under lock bars 70 and extend upwardly away from bone 20, before reversing course and turning proximally away from hook 50 around a distal bar 72 of locking bars 70. Cord 40 may extend from distal bar 72 proximally away from hook 50 and then downwardly toward bone 20 before extending distally such that cord 40 goes around a proximal bar 74 of lock bars 70. From a bottom side 75 of proximal bar 74, cord 40 may extend upwardly and distally toward a top side 73 of distal bar 72. Cord 40 may extend upwardly over and/or contact top side 73 with a first cord portion 80 thereof while a second cord portion 82 may contact an opposite side of first cord portion 80 relative to top side 73. Cord 40 may extend from top side 73 distally toward hook 50 then downwardly toward bone 20 while contacting bar 72. First cord portion 80 and second cord portion may contact each other as cord 40 extends proximally from bar 72 away from hook 50. Proximal end 48 of cord 40 may be located on top of a distally extending portion 49 extending away from locking bars 70 around bone 20 toward hook 20. Proximal end 48 may be pulled by a user in a direction opposite from hook 50 to pull cord 40 through and past locking bars 70 as described above. A path of cord 40 past and against bars 70 may provide a frictional resistance to a release of cord 40 from bars 70 such that cord 40 may be tightened and such position retained to hold fractured portions of bone 20 for a period of time, or may remain in place, to allow a reduction of a fracture.

As described, system 10 may be utilized for fixating or reducing bone 20 and a process for such fixating or reducing is described as follows.

Figure 5:
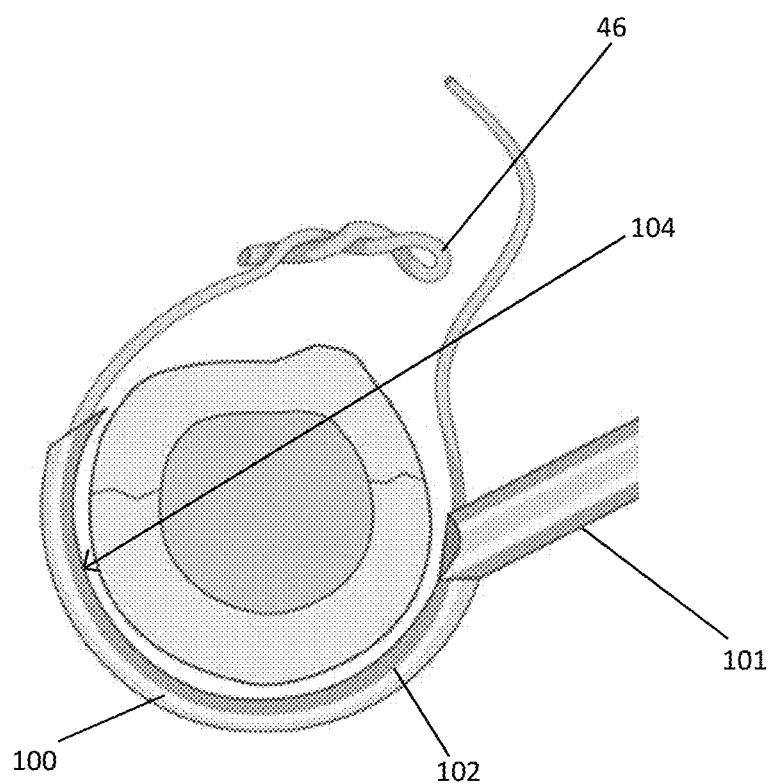
FIG. 5 is a side view of a passer including the cord of FIG. 1 received in a cavity therein.
Figure 6:
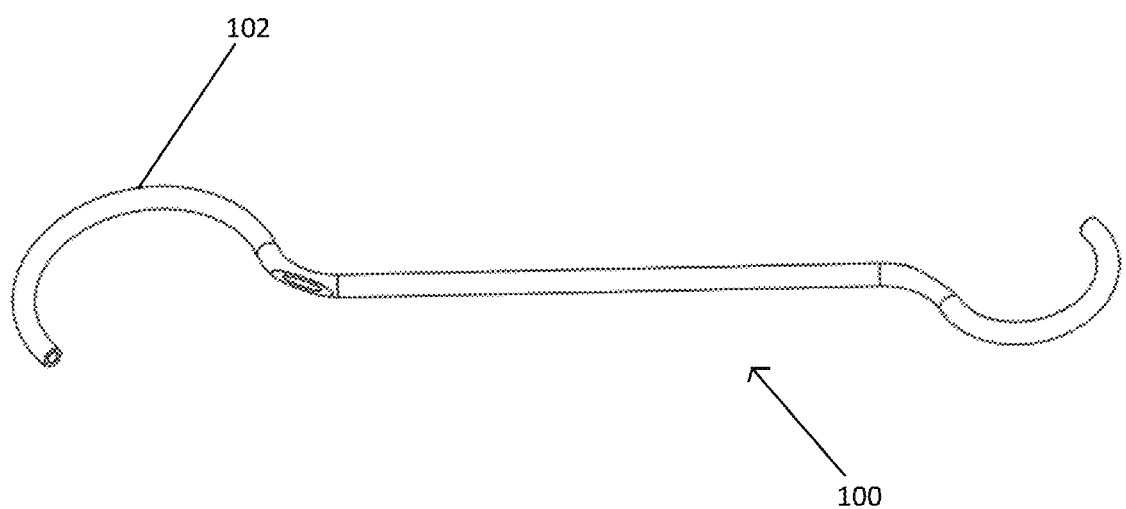
FIG. 6 is a side view of the passer of FIG. 5.
Figure 7:
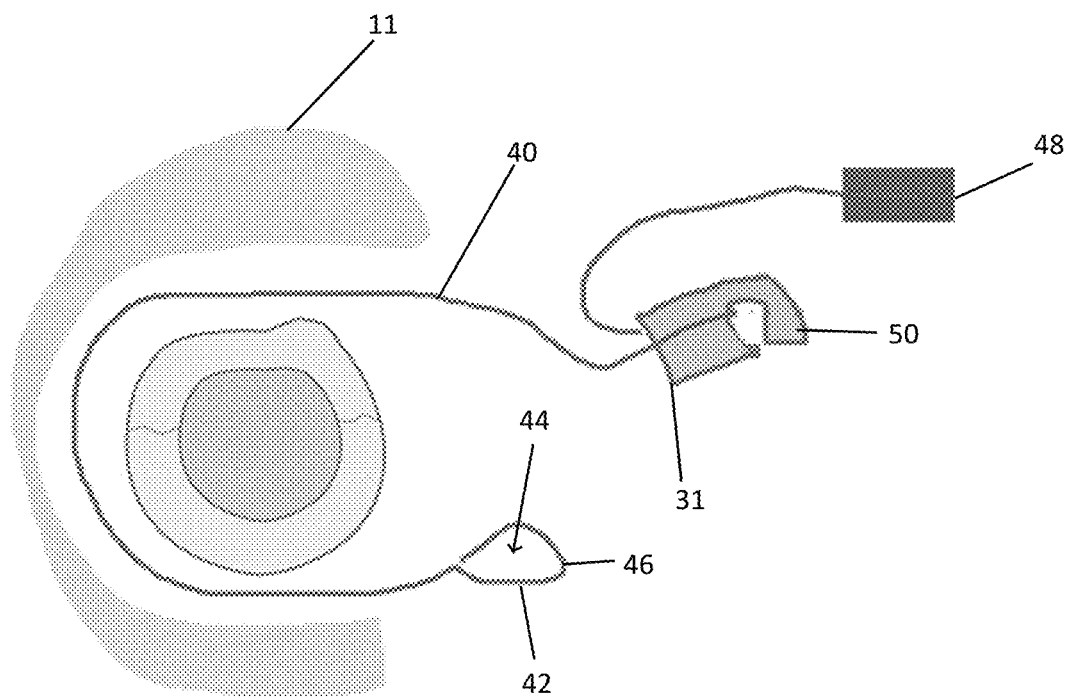
FIG. 7 is a side view of the system of FIG. 5 including the cord attached to a proximal end of the buckle and a loop of the cord configured to be attached to the buckle.

Cord 40 may be passed around bone 20 and under tissue and muscle 11 using a passer 100 as depicted in FIGS. 5-7. Passer 100 may have a curved extension portion 102 having a cavity 104 along an inner circumferential side for receiving cord 40 prior to a procedure such that passer 100 holding cord 40 in cavity 104 may be manipulated around bone 20 and under tissue and muscle 11, such that distal end 46 may be passed to an opposite side of bone 20 relative to a handle portion 101 of passer 100. Passer 100 may be removed from bone 20 with cord 40 remaining around bone 20 such that distal end 46 and proximal end 48 may be located on a same side of bone 20.

Figure 8:
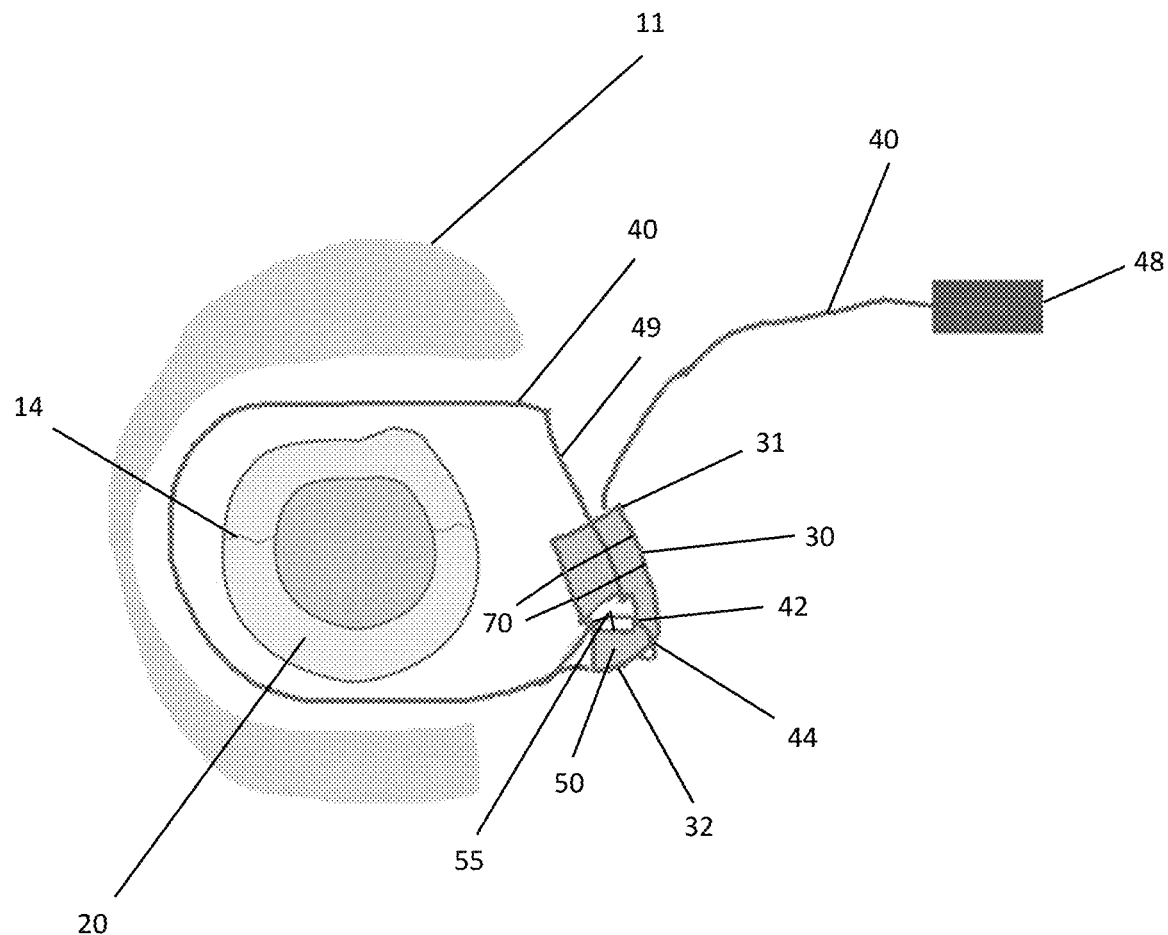
FIG. 8 is a side view of the system of FIG. 7 with the buckle and loop attached to each other.
Figure 9:
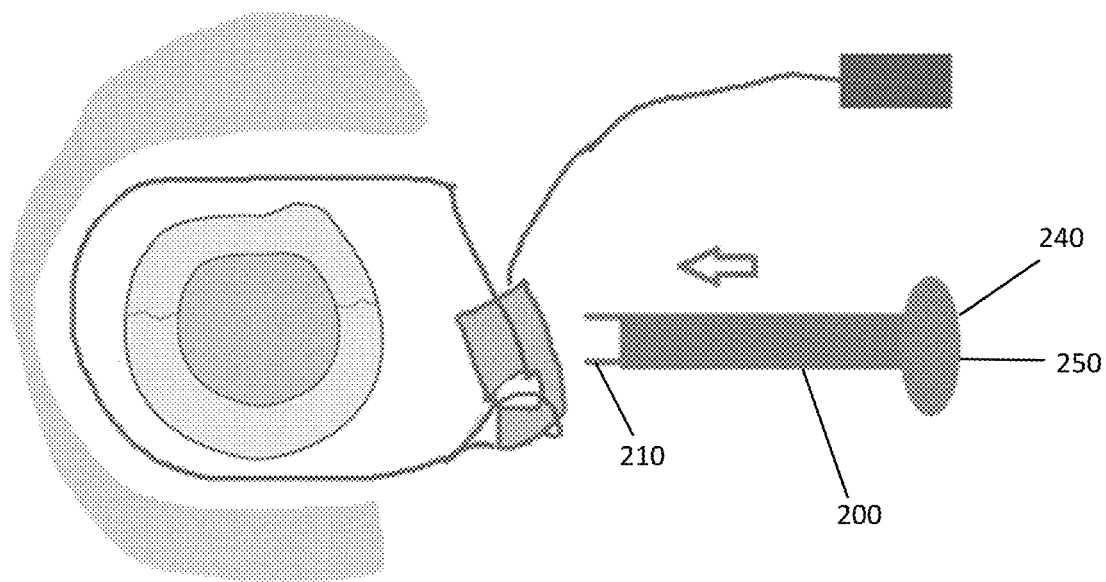
FIG. 9 is a side view of the system of FIG. 8 further including a tensioner.
Figure 10:
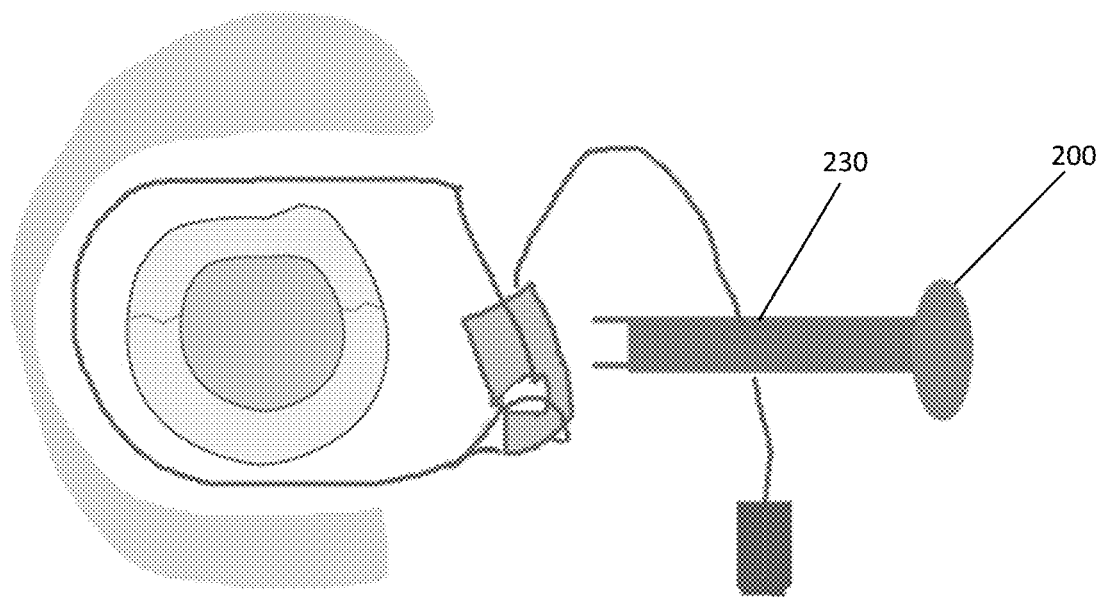
FIG. 10 is a side view of the system of FIG. 9 with the proximal end of the cord received through a passage of the tensioner.
Figure 11:
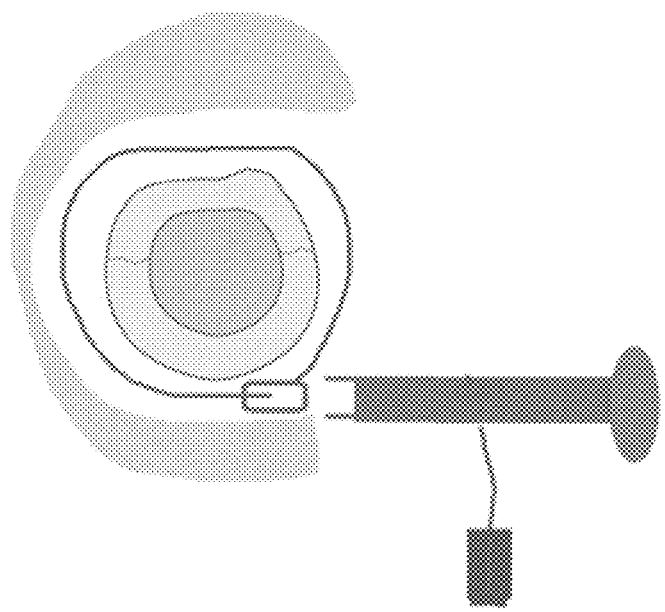
FIG. 11 is a side view of the system of FIG. 10 with the tensioner aligned to connect to the buckle.

As depicted schematically in FIGS. 7-9, loop 42 of cord 40 may be connected to hook 50 and received in cavity 55. Cord 40 may be threaded around and connected to lock bars 70 as described above, depicted in FIGS. 1-3, and depicted schematically in FIGS. 7-9. A user may tighten cord 40 around bone 20 to reduce a fracture 14 of bone 10 by holding buckle 30 while pulling proximal end 48.

Figure 14:
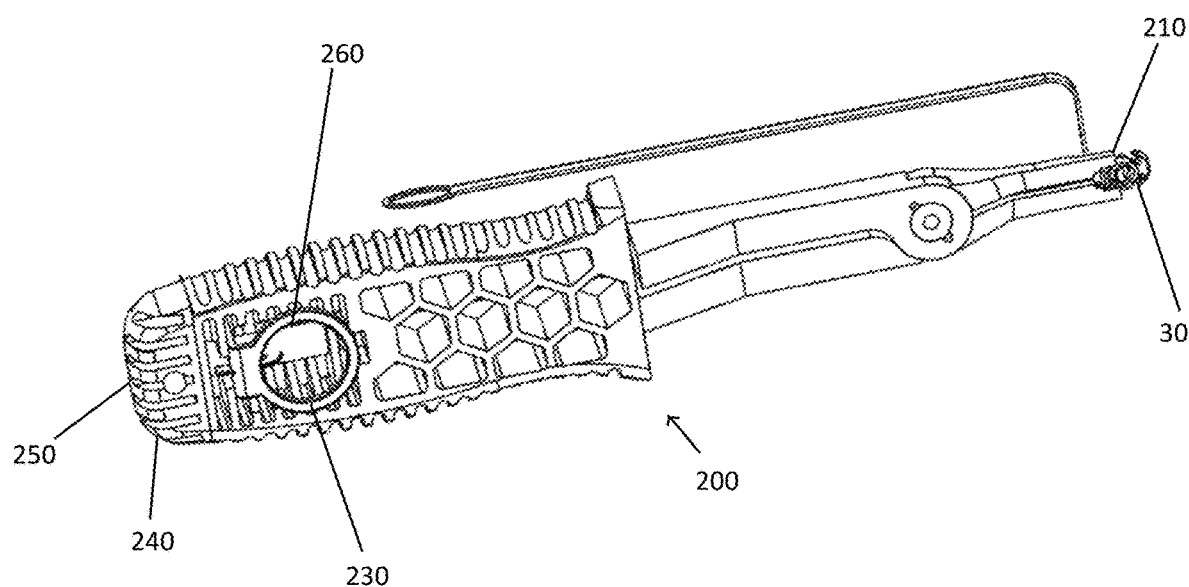
FIG. 14 is a perspective view of the tensioner of FIG. 13.

In an example, buckle 30 may include a pair of slots 35 located on opposite axial or longitudinal sides of buckle 30 relative to bone 20 as depicted in FIG. 1. Slots 35 may be configured (e.g., shaped and dimensioned) to receive arms 210 of a tensioner 200 depicted in FIG. 14 and depicted schematically in FIGS. 9-13. After cord 40 is passed around bone 20 and connected to buckle 30, proximal end 48 of cord 40 may be passed through a receiving passage 230 in tensioner 200 to allow cord 40 to be drawn or pulled by tensioner 200. Arms 210 may be received in slots 35 to connect tensioner 200 to buckle 30.

Figure 12:
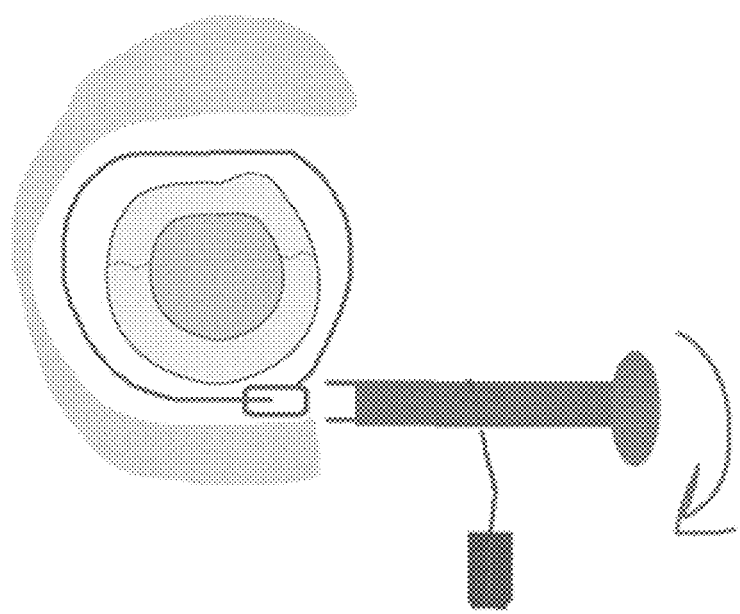
FIG. 12 is a side view of the system of FIG. 11 showing the direction of rotation of a handle of the tensioner to draw the cord to tighten the cord relative to the buckle and the bone.
Figure 13:
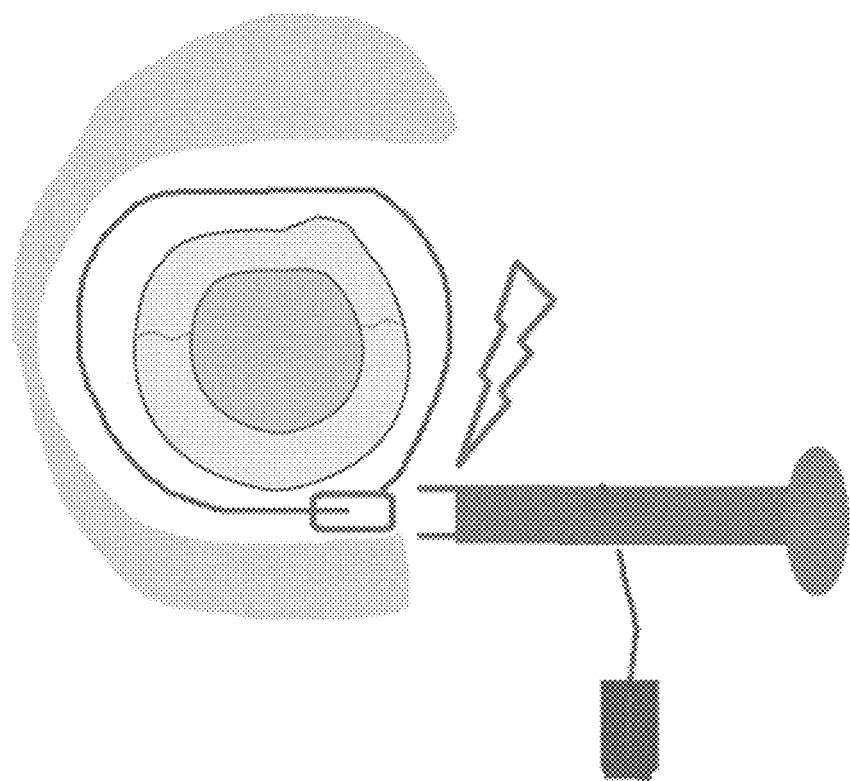
FIG. 13 is a side view of the system of FIG. 11 showing the cord being cut.

A handle 240 of tensioner 200 may be rotated by a user to cause the drawing of cord 40 by tensioner 200 away from bone 20 and toward a proximal end 250 of tensioner 200 as depicted in FIG. 12. A force provided on cord 40 by the drawing by tensioner 200 may pull cord 40 around lock bars 70 of buckle 30 to tighten cord 40 around bone 20, as described above, such that cord 40 is held at a particular tightness by friction provided by the path of cord 40 around lock bars 70 to allow a reduction of fracture 14, for example.

Tensioner 200 may include a rod 260 connected to handle 240 and including passage 230 to provide the drawing of cord 40 as described.

After cord 40 is tightened a desired amount around bone 20, e.g., when fracture 14 is placed in a desired position as determined by a user or surgeon, cord 40 may be cut such that proximal end 48 is at or adjacent to proximal end 31 of buckle 30 such as depicted in FIG. 1. Any sutures in the area around the fracture may be closed with buckle 30 and cord 40 remaining.

As indicated, buckle 30 and cord 40 may be utilized to for temporary fixation of a bone (e.g., fracture 14 of bone 10) with the buckle and cord being removed after a period of time (e.g., after the bone has healed) or buckle 30 and cord 40 may remain in vivo after the bone has healed. In an example, a bone plates may be placed over a tape (e.g., cord 40), to allow such a plate to be attached to appropriate portions of a bone (e.g., bone 10) cord 20 and buckle 30 are in place to reduce a fracture (e.g., fracture 14) Cord 40 may be cut and removed if the plate is adequate to hold the bone and cord 40 is not also needed. Such plates may also be applied to a bone other than over a cord to hold such bone to reduce a fracture, for example. Such plates or other surgical hardware may also remain in vivo with or without such a buckle and cord (e.g., buckle 30 and cord 40) hardware to stabilize a bone (e.g., a fracture 14) during a consolidation thereof.

In an example, multiple instances of a buckle and cord (e.g., buckle 30 and cord 40) may be utilized to fixate a fracture (e.g., fracture 14) or otherwise to hold a bone (e.g., bone 10) together at various longitudinal points along such a bone. A fracture may thus be segmentally reduced by incrementally drawing fragments of bone (e.g., bone 10) together. Such fracture reduction may be a dynamic operation and forces may need to be redirected due to an often-complex geometry of mating faces that may be adjusted and moved back together by manipulating a series of buckles and cord (e.g., multiple instances of buckle 30 and cord 40).

In another example not depicted, a holding member (not shown) may be used in place of tensioner 200 with the holding member including arms configured as arms 210 described above for tensioner 200, but not including a mechanism for drawing cord 40. Instead the holding member may include a holding portion extending away from the arms to allow a user to hold the holding member thereby holding buckle 30 via the arms. While holding the holding member to hold the buckle a user may pull proximal end 48 of cord 40 to secure cord 40 around bone 20 to reduce fracture 14, for example.

Figure 15:
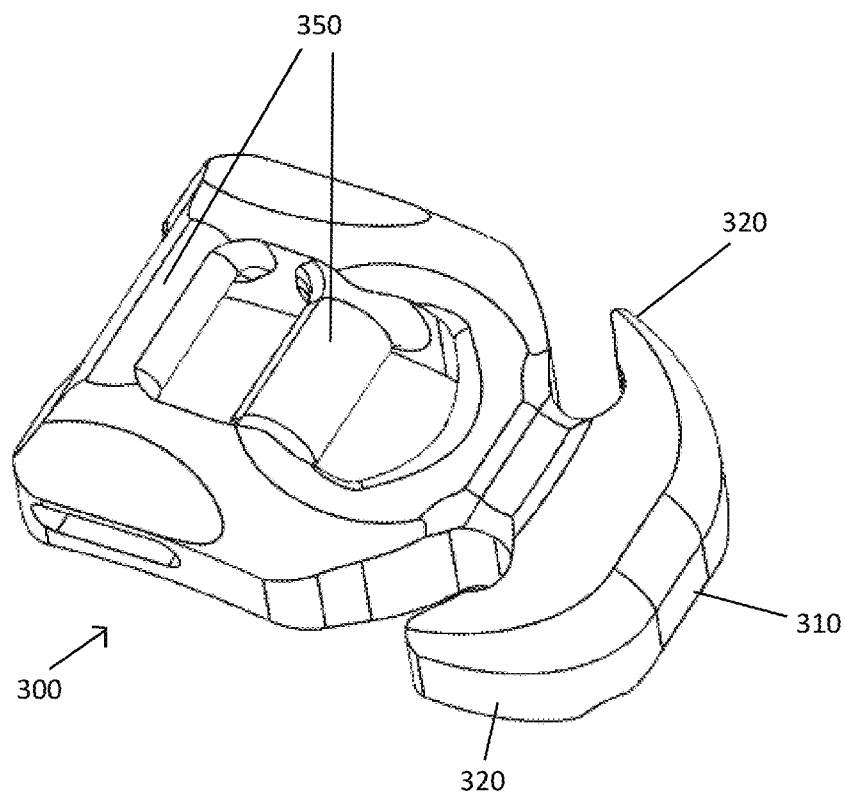
FIG. 15 is a perspective view of another example of a buckle useful in place of the buckle of FIG. 1.
Figure 16:
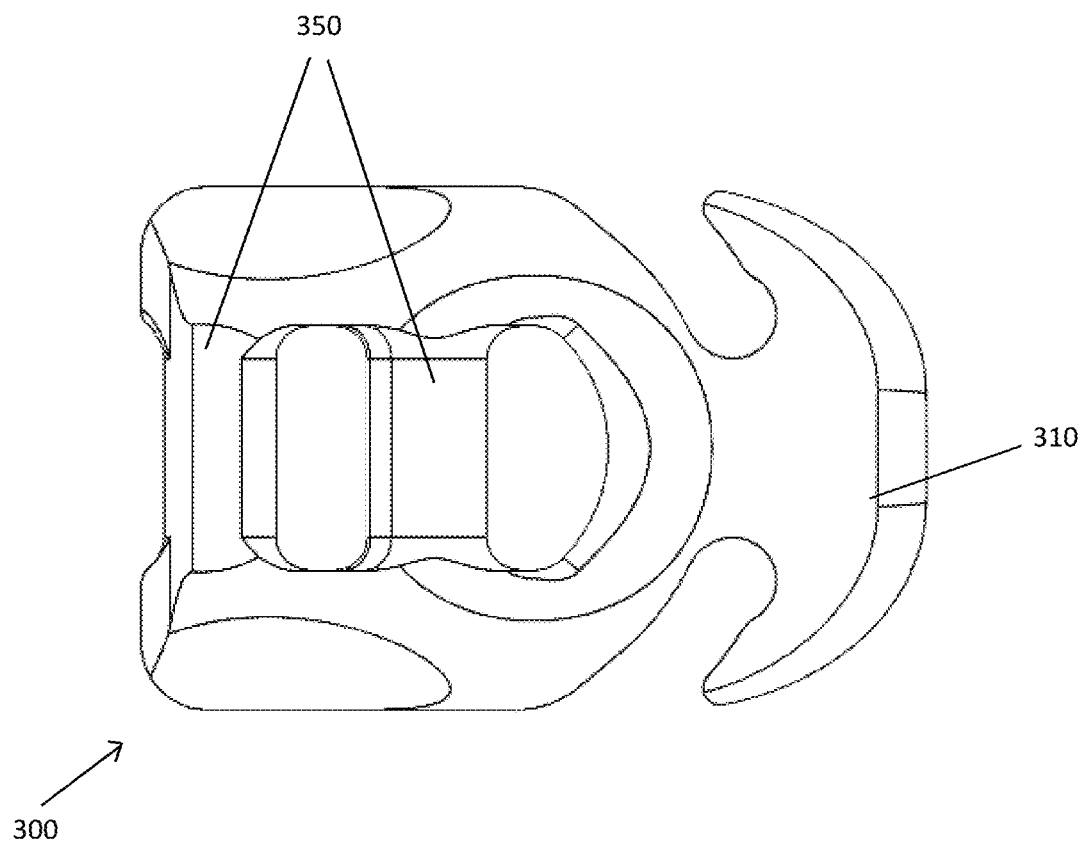
FIG. 16 is a top view of the buckle of FIG. 15.

In another example depicted in FIGS. 15-16, a buckle 300 may be utilized in place of buckle 30 described above and may include a hook 310 having two outwardly facing prongs 320 configured to be attached to loop 42 of cord 40. Lock bars 350 may be utilized to connect to cord 40 as described above for lock bars 70.

Figure 17:
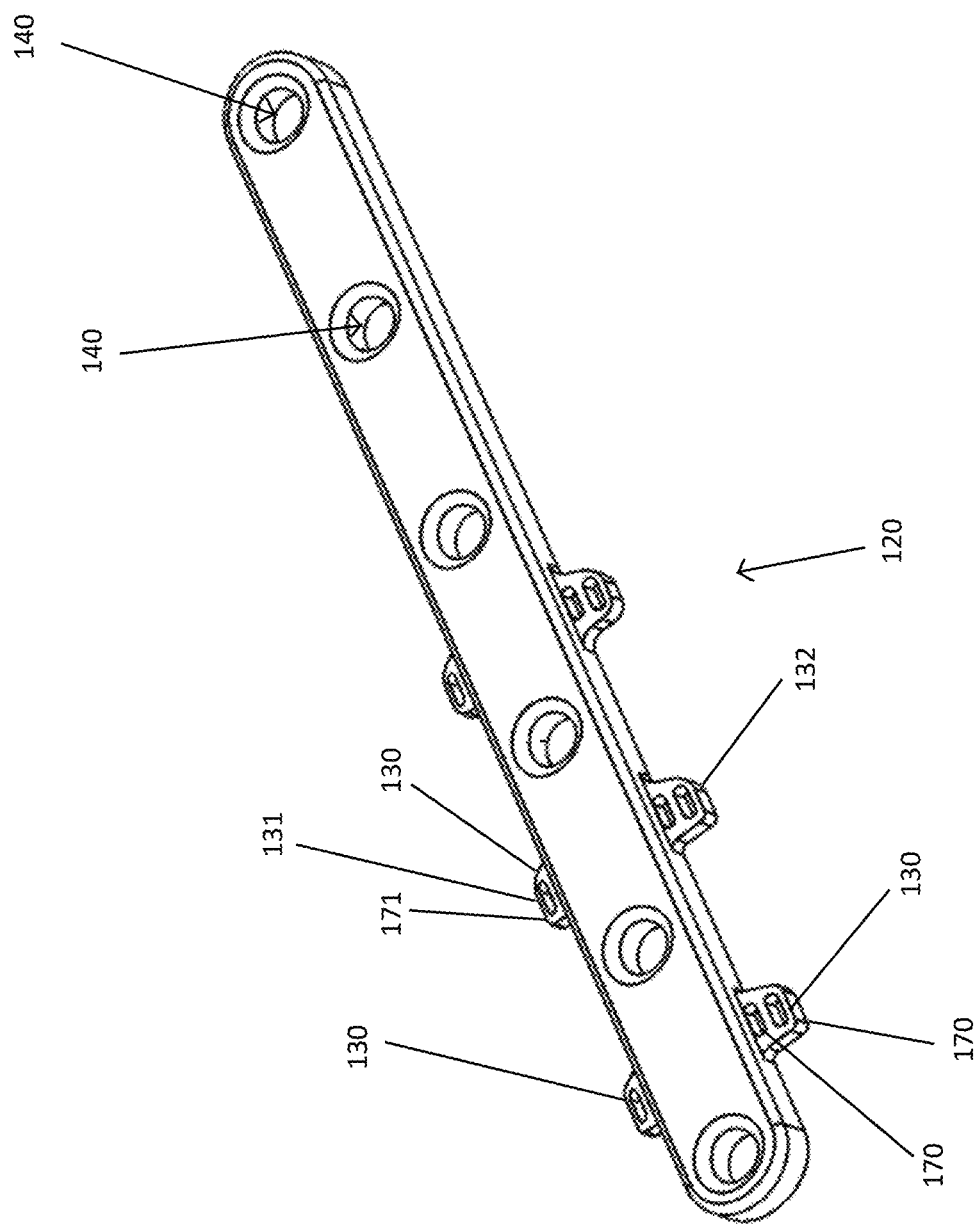
FIG. 17 is a perspective view of a plate having a plurality of buckles in accordance with the present invention.
Figure 18:
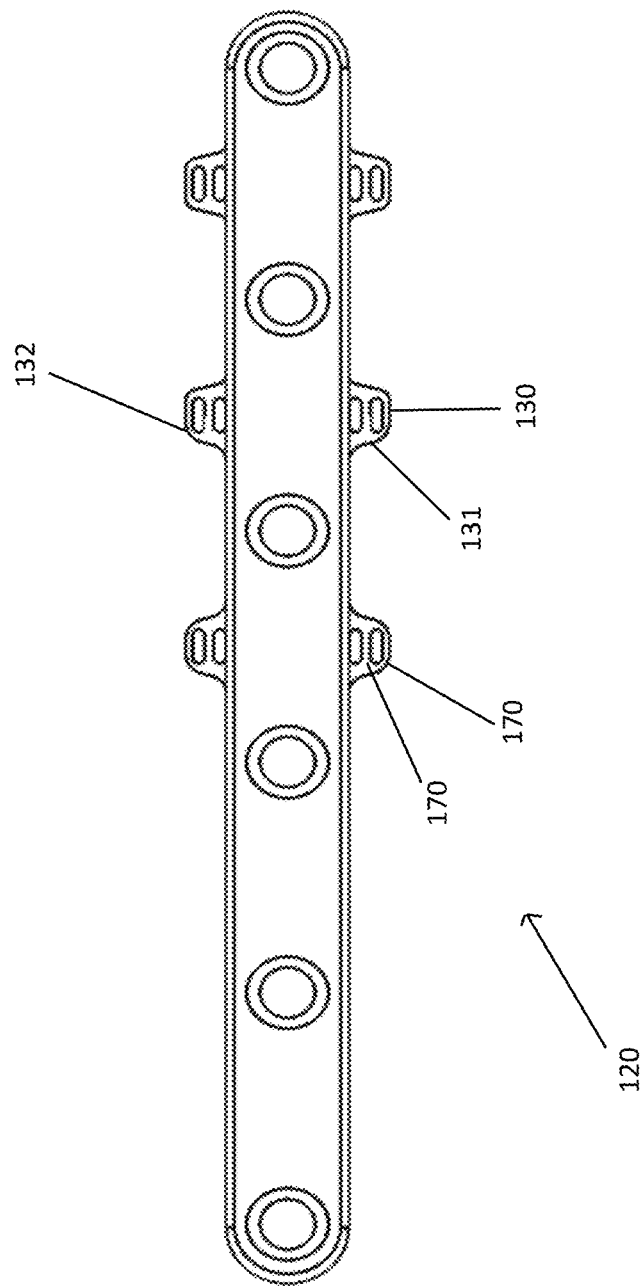
FIG. 18 is a top view of the plate of FIG. 17.

In an example depicted in FIGS. 17-18, a plate 120 may include buckles 130 having lock bars 170 and a plurality of openings 140 for receiving screws therethrough to allow plate 120 to be fastened to a bone (e.g., bone 10). A cord (e.g., cord 40) may be attached to a first buckle 131 and a second buckle 132 of buckles 130 as described above for cord 40 being attached to buckle 30. In an undepicted example, second buckle 132 may be replaced by a hook, similar to hook 50 described above, and a cord (e.g., cord 40) may be attached to lock bars 171 of buckle 131 and the hook as described for lock bars 70, hook 50 and cord 40. Multiple instances of such buckles may be present along a length of a plate (e.g., plate 120). Each instance of a cord (e.g., cord 40) attached to opposing buckles (e.g., first buckle 131 and second buckle 132) may be tensioned at a same or differing amount around a bone (e.g., bone 10) to achieve a particular therapeutic purpose for reducing a fracture (e.g., fracture 14) Screws may be inserted though openings 140 after one or more such cords are attached to one or more of buckles 130 along plate 120 to secure and reduce a fracture in a bone (e.g., bone 10).

Figure 19:
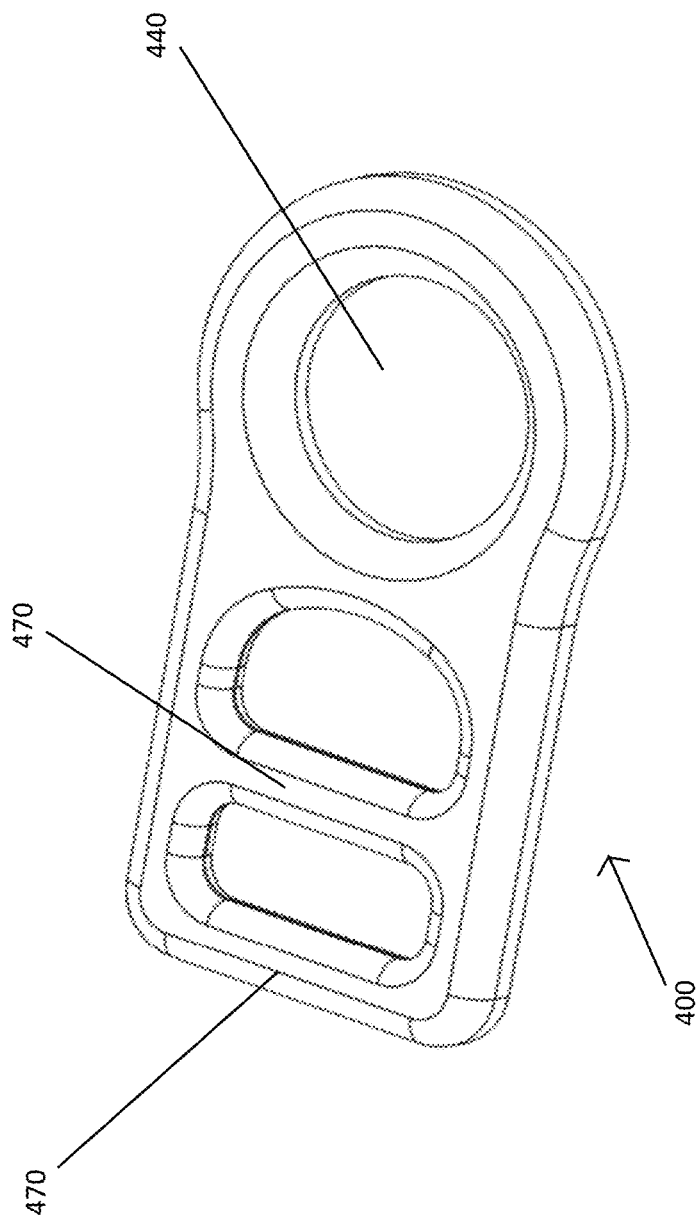
FIG. 19 is a perspective view of a washer having a plurality of lock bars in accordance with the present invention.

In an example depicted in FIG. 19, a washer 400 may include lock bars 470 and an opening 440 for receiving screws therethrough to washer 400 to be fastened to a bone (e.g., bone 10). Washer 400 may be located at a desired point on a bone (e.g., bone 10) where no other hardware is placed or washer 400 may be located on a plate such that opening 440 is aligned with a hole of the plate to allow a screw to pass through opening 440 and the opening of the plate to connect washer 400 to such plate. A cord (e.g., cord 40) may be attached to lock bars 470 and lock bars or a hook of another washer, buckle or plate to hold portions of a bone (e.g., bone 10) together to reduce a fracture, for example. In other examples, lock bars may be integrated into other fracture fixation hardware, e.g., washers, plates, toothed washers, and bone anchors. Buckles in these cases may have both ends of a cord (e.g., cord 40) secured or the cord may be secured between two discrete pieces of hardware (e.g., first buckle 131, second buckle 132, and washer 400).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A fracture fixation system comprising: a connector having a proximal end for connecting to a first end of a cord configured to extend around a bone to provide fixation to a fracture of the bone, said proximal end comprising a plurality of lock bars bounding slots for engaging the cord to tighten the cord to provide the fixation of the fracture; said connector having a distal connecting end opposite said connector relative to said proximal end for attaching to a second end of said cord extending around the bone; said distal connecting end comprising a hook or loop; and said fracture fixation system further comprises a tensioner engaged with slots on opposite longitudinal sides of said connector to hold said connector to allow a user to provide tension to the cord to fixate the fracture, wherein said slots on opposite longitudinal sides of said connector are aligned longitudinally relative to the connector and are configured to engage arms of said tensioner.

2. The system of claim 1 wherein said tensioner comprises a handle connected to a rod having a passage to receive the cord such that a rotation of the handle provides a tension on the cord to fixate the fracture.

3. The system of claim 1 wherein a first lock bar of said plurality of lock bars comprises a cross-sectional tear drop shape.

4. The system of claim 1 wherein the cord is threaded around the lock bars and tightened such that the cord is held at a particular tightness to allow the fixation of the fracture.

* * * * *